US005447966A

United States Patent [19]

Hermes et al.

[11] Patent Number: 5,447,966

[45] Date of Patent: Sep. 5, 1995

[54] TREATING BIOABSORBABLE SURGICAL ARTICLES BY COATING WITH GLYCERINE, POLALKYLENEOXIDE BLOCK COPOLYMER AND GELATIN

[75] Inventors: Matthew E. Hermes, Easton; Ross R. Muth, Brookfield; Darel L. Gustafson, Shelton, all of Conn.

[73] Assignee: United States Surgical Corporation, Norwalk, Conn.

[21] Appl. No.: 193,511

[22] Filed: Feb. 8, 1994

Related U.S. Application Data

[63] Continuation of Ser. No. 740,067, Aug. 5, 1991, abandoned, which is a continuation-in-part of Ser. No. 529,740, May 22, 1990, Pat. No. 5,037,429, and a continuation-in-part of Ser. No. 221,308, Jul. 19, 1988, Pat. No. 5,051,272.

[51] Int. Cl.⁶ .............................................. A61L 27/00
[52] U.S. Cl. ..................................... 523/113; 424/423
[58] Field of Search ................ 424/430, 423; 523/103, 523/113

[56] References Cited

U.S. PATENT DOCUMENTS

| | | |
|---|---|---|
| 2,046,320 | 7/1936 | Burbank . |
| 2,374,201 | 4/1945 | Highberger et al. . |
| 2,477,742 | 8/1949 | Hall . |
| 2,507,244 | 5/1950 | Correll . |
| 3,276,448 | 10/1966 | Kronenthal ...................... 128/334 |
| 3,413,079 | 11/1968 | Rich, Jr. . |
| 3,527,225 | 9/1970 | Smith . |
| 3,563,228 | 2/1971 | Seiderman . |
| 3,649,163 | 3/1972 | McCusker . |
| 3,765,917 | 10/1973 | Hijiya et al. . |
| 3,791,388 | 2/1974 | Hunter et al. . |
| 3,896,814 | 7/1975 | Vivien et al. . |
| 3,955,012 | 5/1976 | Okamura et al. . |
| 4,027,676 | 6/1977 | Mattei ............................ 428/262 |
| 4,047,533 | 9/1977 | Perciaccante et al. ............. 428/375 |
| 4,105,034 | 8/1978 | Shalaby et al. ..................... 427/2 |
| 4,167,045 | 9/1979 | Sawyer . |
| 4,185,637 | 1/1980 | Mattei . |
| 4,201,216 | 5/1980 | Mattei . |
| 4,215,693 | 8/1980 | Rothman et al. . |
| 4,264,493 | 4/1981 | Battista . |
| 4,291,013 | 9/1981 | Wahlig et al. . |
| 4,330,561 | 5/1982 | Nemoto et al. . |
| 4,344,967 | 8/1982 | Easton et al. . |
| 4,347,234 | 8/1982 | Wahlig et al. . |
| 4,349,470 | 9/1982 | Battista . |
| 4,374,121 | 2/1983 | Cioca . |
| 4,374,125 | 2/1983 | Newell . |
| 4,378,224 | 3/1983 | Nimni et al. . |
| 4,416,814 | 11/1983 | Battista . |
| 4,433,688 | 2/1984 | Bichon . |
| 4,532,929 | 8/1985 | Mattei et al. . |

(List continued on next page.)

FOREIGN PATENT DOCUMENTS

| | | |
|---|---|---|
| 559952 | 7/1958 | Canada . |
| 1183776 | 3/1985 | Canada . |
| 0159167 | 10/1985 | European Pat. Off. . |
| 169001 | 1/1986 | European Pat. Off. . |

(List continued on next page.)

OTHER PUBLICATIONS

Jones, Factors to consider in fluid-bed processing, Pharmaceutical Technology, Apr. 1985.
Hirschfeld, et al., Granulation and Drying in Vacuum Fluid Bed Systems, etc., Drugs Made in Germany, vol. 32, No. 3 (1989), pp. 3-8.

(List continued on next page.)

Primary Examiner—Thurman K. Page
Assistant Examiner—Peter F. Kulkosky

[57] ABSTRACT

An absorbable composition useful for treating absorbable surgical devices to render the same storage stable and/or to enhance delivery of the article and/or a medico-surgically useful substance to a wound. The preferred composition includes collagen or a derivative thereof, a plasticizer and a surfactant.

13 Claims, No Drawings

U.S. PATENT DOCUMENTS

| | | |
|---|---|---|
| 4,552,760 | 11/1985 | Murakami et al. . |
| 4,572,906 | 2/1986 | Sparkes et al. . |
| 4,587,268 | 5/1986 | Pfirrmann . |
| 4,600,533 | 7/1986 | Chu . |
| 4,604,379 | 8/1986 | Twardowski et al. . |
| 4,615,697 | 10/1986 | Robinson . |
| 4,690,816 | 9/1987 | Hata et al. . |
| 4,698,376 | 10/1987 | Asmussen et al. . |
| 4,703,108 | 10/1987 | Silver et al. . |
| 4,705,820 | 11/1987 | Wang et al. . |
| 4,711,241 | 12/1987 | Lehmann . |
| 4,711,783 | 12/1987 | Huc et al. . |
| 4,744,988 | 5/1988 | Brox . |
| 4,747,848 | 5/1988 | Maini . |
| 4,749,689 | 6/1988 | Miyata et al. . |
| 4,774,091 | 9/1988 | Yamahira et al. . |
| 4,774,227 | 9/1988 | Piez et al. . |
| 4,778,676 | 10/1988 | Yang et al. . |
| 4,780,316 | 10/1988 | Brox ......................... 424/456 |
| 4,784,659 | 11/1988 | Fleckenstein et al. . |
| 4,789,663 | 12/1988 | Wallace et al. . |
| 4,795,467 | 1/1989 | Piez et al. . |
| 4,803,075 | 2/1989 | Wallace et al. . |
| 4,837,285 | 6/1989 | Berg et al. . |
| 4,837,379 | 6/1989 | Weinberg ......................... 424/423 |
| 4,839,345 | 6/1989 | Doi et al. . |
| 4,841,962 | 6/1989 | Berg et al. . |
| 4,842,575 | 6/1989 | Hoffman, Jr. et al. . |
| 4,844,067 | 7/1989 | Ikada et al. . |
| 4,849,141 | 7/1989 | Fujioka et al. . |
| 4,849,246 | 7/1989 | Schmidt . |
| 4,875,479 | 10/1989 | Belykh et al. . |
| 4,879,108 | 11/1989 | Yang et al. . |
| 4,882,137 | 11/1989 | Staples et al. ......................... 424/424 |
| 4,888,366 | 12/1989 | Chu et al. . |
| 4,935,243 | 6/1990 | Borkan et al. . |
| 4,950,483 | 8/1990 | Ksander et al. . |
| 4,950,699 | 8/1990 | Holman . |
| 4,969,912 | 11/1990 | Kelman et al. . |
| 4,970,298 | 11/1990 | Silver et al. . |
| 4,975,526 | 12/1990 | Kuberasampath et al. . |
| 4,980,403 | 12/1990 | Bateman et al. . |
| 4,987,031 | 1/1991 | Tatematsu et al. . |
| 4,992,100 | 2/1991 | Koepff et al. . |
| 4,992,226 | 2/1991 | Piez et al. . |
| 5,001,169 | 3/1991 | Nathan et al. . |
| 5,007,925 | 4/1991 | Tsilibary et al. . |
| 5,037,429 | 8/1991 | Hermes et al. . |
| 5,051,272 | 9/1991 | Hermes et al. ......................... 427/2 |
| 5,064,941 | 11/1991 | Davison . |
| 5,112,619 | 5/1992 | Thakkar et al. . |
| 5,114,720 | 5/1992 | Littell et al. . |

FOREIGN PATENT DOCUMENTS

Olsen, Batch Fluid Bed Processing Equipment—A Design Overview, Pharmaceutical Technology, Jan. 1989, pp. 34–36 and Jun. 1989, pp. 38–50.

The New Generation of Glatt Fluid Bed Dryers and Granulator/Dryers, by Glatt Air Techniques, Inc., 1986-1987.

OTHER PUBLICATIONS

| | | |
|---|---|---|
| 0197506 | 10/1986 | European Pat. Off. . |
| 0128043 | 10/1989 | European Pat. Off. . |
| 0354345A2 | 2/1990 | European Pat. Off. . |
| 2938438A1 | 3/1981 | Germany . |
| 2142824 | 1/1985 | United Kingdom . |

TREATING BIOABSORBABLE SURGICAL ARTICLES BY COATING WITH GLYCERINE, POLALKYLENEOXIDE BLOCK COPOLYMER AND GELATIN

CROSS-REFERENCE TO RELATED APPLICATIONS

This is a continuation or of application Ser. No. 07/740,067, filed on Aug. 5, 1991, now abandoned, which is a continuation-in-part of U.S. application Ser. No. 07/529,740 filed May 22, 1990, now U.S. Pat. No. 5,037,429 and U.S. application Ser. No. 07/221,308 filed Jul. 19, 1988, now U.S. Pat. No. 5,051,272 the entire contents of both of these applications being incorporated by reference herein.

BACKGROUND OF THE INVENTION

The present invention relates to a bioabsorbable composition for bioabsorbable articles such as sutures, clips, staples, pins, screws, tacks, sponges, gauzes, implants or prostheses suitable for introduction into a living body. More particularly, the present invention is directed to a bioabsorbable composition associated such as by filling or coating, with a bioabsorbable article so as to protect the article from premature hydrolytic degradation upon storage and/or to facilitate delivery of the article and associated therapeutic agents to a wound site.

This invention provides a method for improving the storage stability of polymeric articles having an inherent tendency to undergo degradation when exposed to water or a humid atmosphere, probably as a result of hydrolysis. More particularly, the invention is directed to improving the storage stability of articles and devices such as absorbable surgical sutures, clips, staples, implants, protheses and the like, fabricated from polymers which are susceptible to hydrolytic degradation, notably, polymers and copolymers of glycolic acid (i.e., hydroxyacetic acid), the cyclic dimer of glycolic acid ("glycolide"), lactic acid, the cyclic dimer of lactic acid ("lactide") and related monomers.

Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and, 4,523,591; U.K. Patent No. 779,291; D K Gilding et al., "Biodegradable polymers for use in surgery—polyglycolic/poly(lactic acid) homo- and co-polymers: 1, *polymer*, volume 20, pages 1459–1464 (1979), and D. F. Williams (ed.), *Biocompatibility of Clinical Implant Materials*, Vol. II, ch. 9: "Biodegradable Polymers" (1981). The biodegradability of these polymers/copolymers is believed to be due to the hydrolytic attack of their ester linkages by aqueous body fluids although the exact mechanism involved has been a matter of speculation.

An absorbable device (e.g., an absorbable suture or other aqueous body fluid-absorbable article) may experience prolonged storage before use, e.g., periods of several months and sometimes even several years. In order to prevent water or humidity in the storage environment from contacting the article and compromising its in vivo strength to the point where the article is no longer serviceable, it is common practice to package the article in an essentially moisture impermeable enclosure. However as noted in U.S. Pat. Nos. 3,728,839 and 4,135,622, any package material which prevents the entry of moisture will also prevent the escape of moisture. Thus, any moisture associated with or absorbed by the article at the time it is packaged will tend to remain in the package for the entire period of its storage.

According to aforesaid U.S. Pat. Nos. 3,728,839 and 4,135,622, the in-vivo strength of polyglycolic acid surgical elements such as sutures undergoes significant deterioration on long term standing in the package, even on exposure of the contents to very small amounts of water for very short periods of time, e.g., 20 minutes or less, just prior to packaging due to the aforenoted tendency of a moisture impervious package to seal the moisture in with the suture.

To prevent hydrolytic degradation of the suture or to minimize its extent, U.S. Pat. Nos. 3,728,839 and 4,135,622 disclose removing moisture from the suture before sealing the package so that virtually no water remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°–188° for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated.

Considered in their entirety, these operations for improving the storage stability of absorbable sutures and other surgical devices which are susceptible to hydrolytic degradation amount to a time consuming, expensive and relatively complex solution to the storage stability problem.

In addition, although coating braided sutures has long been known and practiced, see, e.g., U.S. Pat. No. 3,297,033, prior to the present invention it has been difficult to coat solid bioabsorbable articles, notably fairly rigid articles such as clips, tacks, staples, because the coatings often tend to flake or peel off the coated article. This is especially a problem when the article is being implanted in a living body, e.g., by firing from instruments. Provision of an adherent bioabsorbable coating upon surgical articles is especially desirable because certain additives can be incorporated into the coating, such as various growth factors, which could not withstand processing conditions for forming the bioabsorbable articles themselves.

SUMMARY OF THE INVENTION

Accordingly, it is an object of the present invention to overcome the aforenoted disadvantages associated with the storage stabilizing method described in U.S. Pat. Nos. 3,728,839 and 4,135,622.

It is also an object of the present invention to provide an improved adherent bioabsorbable coating upon a bioabsorbable surgical article which will not flake or peel off the article, e.g., while being implanted into a living body.

It is another object of the present invention to provide an improved bioabsorbable coating upon a bioabsorbable surgical device which can successfully serve as a carrier for ingredients which cannot be successfully incorporated into the bioabsorbable articles themselves.

It is yet another object of this invention to provide a method for improving the storage stability of a polymeric article susceptible to hydrolysis, e.g., an absorbable surgical article such as a suture based in whole or in part on a polyester polymer or copolymer such as polyglycolic acid, lactide-glycolide copolymer, polydioxanone, polytrimethylene carbonate, polyalkylene glycol, polycaprolactone, their copolymers, etc., which does not require a diminution pre-packaged moisture content of the article or temporary storage of the article in an artificially-maintained bone dry environment prior to completion of the packaging operation.

These and other objects are accomplished by the present invention which is directed to an absorbable coating composition useful for coating or filling absorbable surgical devices, the absorbable composition comprising:

(i) a storage stabilizing amount of collagen or a derivative of collagen;
(ii) a plasticizer dispersed or dissolved in (i) the collagen or derivative thereof; and
(iii) a surfactant dispersed or dissolved in (i) the collagen or derivative thereof or in (ii) the plasticizer. In certain instances the coating composition may just comprise collagen or a derivative thereof, with the plasticizer and/or surfactant being optional.

The present invention is also directed to a method for improving the storage stability of a bioabsorbable surgical article which comprises applying by coating, filling or other appropriate means of association, a storage stabilizing amount of the enumerated composition supra to the surgical article, as a storage stabilizing agent therefor.

The term "filled" as used herein refers to the association of an article with a composition in which the composition is absorbed into the article, e.g., pores or interstices of the article, is present on the surfaces thereof or a combination of the two.

The term "coated" as used herein refers to the association of an article with a composition in which the composition remains predominantly at or about the outer surfaces of the article. For convenience, the composition and method will be hereafter discussed in terms of "coating" an article. This should not be construed, however, as restricting the invention to coating or excluding other means of associating the composition with a bioabsorbable surgical article such as by filling a braided suture as described in U.S. Pat. No. 5,037,429.

Ordinarily, the stabilizing agent can be applied to the bioabsorbable article without the need to reduce moisture level of the article, either before or after applying the stabilizing agent thereto, to a very low level, e.g., to a state of being bone dry as in U.S. Pat. Nos. 3,728,839 and 4,135,622, since entirely acceptable levels of storage stability can be achieved without resorting to such drastic moisture reduction efforts. Similarly, it is altogether unnecessary to maintain the article in a bone dry environment at any time following its manufacture and preceding the completion of its packaging as in the aforesaid patents. Once the article is contacted with the coating composition which will thereafter be retained upon the bioabsorbable article by adhering to its surfaces, the article can be immediately packaged and sterilized since all that is necessary to effect its long term hydrolytic stability will have been accomplished by the coating application operation. Such being the case, the storage stabilizing method of the present invention possesses the advantages of simplicity, economy and a level of production efficiency unattainable by tho storage stabilizing method described in U.S. Pat. Nos. 3,728,839 and 4,135,622.

In addition to imparting an enhanced degree of storage stability to polymeric articles subject to hydrolytic degradation, practice of the present invention confers other benefits as well. By way of example only, it has been found that when the composition is coated onto a rigid article, the coating will not flake or peel off the article, notably when the article is being implanted in a living body such as by firing from an appropriate mechanical instrument. Indeed, coated articles in accordance with the invention have been fund to achieve desirably consistent firing and placement characteristics when implanted by firing from a mechanical instrument. Moreover, since the hygroscopic compounds useful in the practice of this invention are generally capable of dissolving a number of medico-surgically useful substances, they can be used as vehicles to deliver such substances to a wound or surgical site at the time the bioabsorbable surgical device is introduced into the body.

DETAILED DESCRIPTION OF THE INVENTION

A characteristic which the polymeric articles to be coated with a coating composition in accordance with this invention share in common is their relatively high susceptibility to undergoing destructive hydrolysis over a period of storage. Generally, this is an inherent characteristic of polymers and copolymers possessing a significant number of short-chain polyester linkages or other readily hydrolyzable linkages in their structure as, for example, is the case with polyglycolic acid, lactide-glycolide polymers, polydioxanone, polyalkylene glycols, polytrimethylene carbonate, polycaprolactone, their copolymers, and related materials. Implant devices formed from glycolide-lactide copolymers are especially suited for being coated in accordance with the present invention. The invention is useful for application to absorbable sutures both of the monofilament and multifilament type (e.g., those of the braided variety which are especially hygroscopic) fabricated from polymers and copolymers of this kind, and applicable to other types of surgically useful articles as well, e.g., those disclosed in U.S. Pat. No. 4,135,622, including without limitation, absorbable surgical clips, staples, pins, tacks, sponges, gauze, implants and prostheses for reconstructing bone tissue, blood vessels, and so forth.

Moreover, because of the desirable ability to deliver medico-surgically useful substances to a wound, it may also be desirable to apply the coating to non-absorbable implants such as permanent orthopedic implants, e.g., joint implants, tendon and ligament augmentation devices, vascular grafts, etc.

Collagen which can be used as the storage stabilizing agent in the coating composition of the present invention is available in various forms. A description of collagen is found at Monograph No. 2442 of *The Merck Index, Ninth Edition* (1976) and at Piez, "Collagen": *Encyclopedia of Polymer Science and Enqineerinq, Second*

Edition, Vol. 3 (1985), pages 699–727. For example, the various forms of collagen include type-I collagen which predominates in skin, tendon and bone, type-II collagen which is unique to cartilage and type-III collagen which is found in adult skin.

Derivatives of collagen are also useful as the storage stabilizing agent in the coating compositions of the present invention. One particular derivative of collagen that is especially suitable as the storage stabilizing agent in the coating composition is gelatin, which is obtained by the partial hydrolysis of collagen. A description of gelatin is found at Monograph No. 4217 of *The Merck Index, Ninth Edition* (1976), at Rose, "Gelatin": *Encyclopedia of Polymer Science And Engineering, Second Edition*, Vol. 7 (1987), pages 488–513 and at Viro, "Gelatin": *Kirk-Othmer, Encyclopedia Of Chemical Technology, Third Edition*, Vol. 11 (1980), pages 711–719. Gelatin is considered a derived protein because it is obtained from collagen by a controlled partial hydrolysis forming a heterogeneous mixture of polypeptides, e.g., by boiling skin, tendons, ligaments, bones, etc. with water. Gelatin is soluble in hot water, glycerol and acetic acid, and insoluble in organic solvents.

Properties of gelatin can be controlled by blending selected gelatin extracts derived from collagen. One of these properties is the Bloom strength or Bloom value which is a standard industrial measurement of gel strength and which determines the force in grams required for a plunger to deform the surface of a gel formed from a gelatin solution. The units of this measurement are in grams Bloom and generally fall between the values of about 50 g. to about 330 g. for gelatin. The higher the Bloom strength of gelatin used, the more rigid the ultimate coating of hardened gelatin. Gelatin can be obtained from any number of commercial sources, including Fluka Chemical, Ronkonkoma, N.Y. and Kind & Knox Company, Sioux City, Iowa.

The plasticizer incorporated into the composition of the present invention may be any biocompatible plasticizer or mixture thereof suitable for plasticizing collagen or collagen derived substances. Among suitable plasticizers for use in accordance with the present invention, a water-soluble hygroscopic polyhydroxy compound or ester derivative thereof is contemplated. Among the specific water-soluble hygroscopic polyhydroxy compounds or esters thereof which can be used herein with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred in the case of the preferred gelatin composition. Mixtures of the aforediscussed polyhydroxy compounds or esters, e.g., sorbitol dissolved in glycerol, glycerol combined with monoacetin and/or diacetin, etc., are also useful. Alternatively, the plasticizer can be constituted by just water alone that is added to the collagen or derivative thereof, e.g., gelatin. If appropriate or desirable, one or more thickeners also may be incorporated into the compositions in order to obtain a desired consistency or viscosity. Many kinds of pharmaceutically acceptable thickeners can be utilized including water-soluble polysaccharides, e.g., hydroxypropyl methylcellulose (HPMC) and similar cellulosic materials, polysaccharide gums such as guar, xanthan, and the like, etc. An especially preferred class of thickeners are the saturated aliphatic hydroxycarboxylic acids of up to about 6 carbon atoms and the alkali metal and alkaline earth metal salts and hydrates thereof. Within this preferred class of compounds are those of the general formula

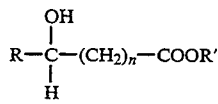

wherein R is hydrogen or a methyl group, R' is hydrogen or a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinbefore, hydrates of these compounds can also be used. Calcium lactate, especially calcium lactate pentahydrate, is a particularly preferred thickener.

The surfactant utilized in the composition of the present invention may be any biocompatible surfactant suitable for promoting wetting and cohesion between the composition and the article. The surfactant is preferably nonionic, more preferably a polyoxyalkylene block copolymer. Suitable low molecular weight polyethylene oxide-polypropylene oxide block copolymers useful in the practice of the present invention include those, for example having the general formula:

wherein x is a number in the range from about 45 to about 90, preferably about 75, y is a number in the range of from about 60 to about 85, preferably about 80, and z is a number in the range of from about 45 to about 90, preferably about 75. Consistent therewith, the low molecular weight polyethylene oxide-polypropylene oxide block copolymers useful in the present invention have molecular weights of from about 5,000 to about 10,000 and preferably from about 7,500 to about 9,000. The synthesis of the block copolymers is readily known and moreover these block copolymers are commercially available and are commercially known as Pluronics. Useful Pluronics in the practice of the present invention are described, for example, in U.S. Pat. No. 2,674,619, U.S. Pat. No. 3,036,118, U.S. Pat. No. 4,047,533 and U.S. Pat. No. 4,043,344.

The surfactant specifically improves wetting of the coating composition upon the surgical device to which the coating is applied, thereby minimizing "beading" i.e., formation of isolated beads of coating upon the coated surgical device. These polyoxyalkylene block copolymers are also marketed under the trade name Poloxamer by BASF Wyandotte, Mich.

It is also contemplated that the surface of the article could be treated so as to promote cohesion and adhesion of the composition to the article. Such treatments include plasma etching, mechanical or chemical etching, mechanical abrasion, etc. One or more surface treatments could be used alone or in conjunction with a surfactant to achieve the desired association of the composition with the article.

The collagen or derivative thereof, plasticizer, and surfactant are preferably mixed in amounts of from about 98% to about 60% by weight of collagen or derivative thereof, about 1% to about 30% by weight of plasticizer and about 0.1% to about 25% by weight of surfactant. More preferably, the components are mixed in proportions of about 90% to about 70% by weight of collagen or derivative thereof, about 5% to about 25% by weight of plasticizer and about 1% to about 20% by weight of surfactant. Most preferably, the components are provided in proportions of about 85% to about 75% by weight of collagen or derivative thereof, about 10% to about 15% by weight of plasticizer and about 5% to about 15% by weight of surfactant.

These levels of ingredients are generally suitable for providing fairly hard films on fairly stiff, unbendable bioabsorbable devices. However, in certain instances, it may be desirable to provide fairly soft films or coatings upon more flexible bioabsorbable articles. In these instances, a comparatively low level of collagen or derivative thereof would be incorporated into the coating, e.g., on the order of about 3% to about 60%, with the remainder of the coating composition being plasticizer along with surfactant, if any.

It is also within the scope of this invention to coat the bioabsorbable device with, or otherwise apply thereto, one or more medico-surgically useful substances, e.g., those which accelerate or beneficially modify the healing process when the device is implanted in the body, e.g., applied to a wound or surgical site. So, for example, the coating herein can be provided with a therapeutic agent which will be deposited in the body. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the bioabsorbable device via the coating of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the bioabsorbable devices herein, e.g., hEGF (urogastrone), TGF-beta, IGF, PDGF, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497; 3,917,824; 3,948,875; 4,338,397; 4,418,691; 4,528,186; 4,621,052; 4,743,679; 4,717,717; 4,861,757; 4,874,746 and 4,944,948, European Patent Application Nos. 046,039; 128,733; 131,868; 136,490; 147,178; 150,572; 177,915 and 267,015, PCT International Applications WO 83/04030, WO 85/003698, WO 85/01284 and WO 86/02271, UK Patent Applications GB 2,092,155 A, 2,162,851 A and GB 2,172,890 A and, "Growth Factors in Wound Healing", Lynch, et al., *J. Clin. Invest.*, Vol. 84, pages 640–646 (August 1989). Of the known HGFs, HEGF, TGF-beta, IGF, PDGF and FGF are preferred, either singly or in combination.

In general, the HGF(s) can be present in the total composition at a level ranging from about 0.1 to about 25,000 micrograms per gram of coating composition, preferably from about 0.5 to about 10,000 micrograms per gram of coating composition, and most preferably from about 1 microgram to about 500 micrograms per gram of coating composition.

In a preferred embodiment of the coating upon a bioabsorbable device of this invention, a coating comprising a surgical wound healing enhancing amount of at least one HGF such as any of those previously mentioned is applied to the device. The coating itself protects the HGF component of the coating composition from excessive degradation or loss of biopotency during storage and as disclosed above, when the device is fabricated from an absorbable resin which is susceptible to hydrolysis, the coating improves the storage stability of the device as well. Where the device itself is not bioabsorbable, i.e., a permanent implant, such protection is, of course, unnecessary.

Application of the composition to the article can be carried out in any number of ways. Thus, for example, the article can be submerged in the coating composition or solution thereof until at least a storage stabilizing amount of the collagen or derivative thereof is acquired or otherwise retained by the article, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the coated article compared to the same type or article which has not been coated.

The foregoing submersion method of coating the bioabsorbable article can be conducted continuously or in batch. Thus, in the case of an absorbable suture, a running length of the suture can be continuously passed through a quantity of the coating composition at a velocity which has been previously determined to provide the necessary degree of coating or contact time of the suture with the coating. As the suture emerges from the coating, it can be passed through a wiper or similar device to remove excess coating prior to the packaging operation. In a batch operation, a quantity of suture is merely submerged within the coating for the requisite period of time with any excess coating being removed from the suture if desired. In the case of a braided suture, it has been found that calendering the suture prior to application of the composition improves receptivity of the suture to the composition and allows the composition to penetrate and fill the interstices of the braid between the yarn and filaments of the braid. As will be appreciated, other types of porous articles may also be treated by filling with the composition.

Alternatively, the coating composition and solutions thereof can be applied by spraying, brushing, wiping, etc., on the surfaces of the articles such that the latter receive and retain at least a storage stabilizing amount of the coating composition. Yet another procedure which can be used to apply the coating composition involves inserting the article in a package containing an effective amount of the composition such that intimate contact between the article and the composition will be achieved.

A preferred method of coating a bioabsorbable article that is substantially rigid, e.g., a pin, clip, tack, prosthetic implant, etc. involves spray coating the device with an aqueous solution of the coating, preferably with an air brush or with a fluidized bed coating technique. The aqueous solution can be prepared with any order of mixing ingredients. In other words, the collagen or derivative thereof, plasticizer and any surfactant can all be mixed together first, with water then being optionally added to form a solution of appropriate concentration. Alternatively, water can be added to the collagen or derivative thereof first, with the plasticizer and any surfactant then being included. Preferably, the water is added to a level of about 1% to about 99% by weight of the resulting solution, more preferably about 5% to about 98% by weight of the resulting solution and most preferably from about 10% to about 97% by weight of the resulting solution.

The spray coating of the coating solution is generally carried out at a temperature of about 30° C. to about 50° C., preferably at about 40° C. As noted above, spraying is preferably carried out with an air brush such as Badger Model 150 available from Badger Air Brush Company, Franklin Park, Ill. Alternatively, a fluidized bed coating technique can be employed, such as fluidized bed coating attained using a Versa Glatt GPCG-1 fluidized bed coater available from Glatt Air Techniques, Ramsay, N.J. Of the various types of fluidized bed coating, top spraying of fluidized articles has been found suitable. Generally, the coating is sprayed to have a thickness upon each article of about 0.01 to about 0.10 mm. after drying, e.g., about 0.05 mm.

After coating, the articles can be left to dry, or alternatively placed within a vacuum chamber to enhance drying. For example, the coated articles can be placed in a vacuum chamber at ambient temperature overnight. The articles are sterilized, such as by exposure to ethylene oxide in a known manner. To facilitate mass production, it may be desirable to equilibrate the moisture content of the coated article, such as by placing the coated articles in an environmental chamber having a controlled dew point of e.g., about +10° C. to about −25° C., more preferably about 0° C. to about −20° C., and most preferably at about −10° C. to about −15° C., for about 96 to about 336 hours. Such a moisture content in the atmosphere will typically result in a stabilized surgical article possessing an amount of moisture in the range of from about 0.3 to about 1.5 weight percent or more. Moisture levels within this range, while not tolerated by the packaging method and packaged synthetic surgical element of U.S. Pat. Nos. 3,728,839 and 4,135,622, have no appreciably deleterious effect on the long term in vivo strength of articles coated in accordance with the present invention, Thus, the coated article agent can, if desired, be packaged at relatively high levels of relative humidity, e.g., those just mentioned. Where the articles are to be included in a mechanical instrument, the coated articles are preferably assembled into the instrument, sterilized in the instrument, and moisture equilibrated prior to sealing the package. As is known, bioabsorbable articles should be packaged in a substantially moisture impervious package such as a foil laminate pouch.

Whatever the contacting procedure employed, it is necessary that the article being treated acquire a storage stabilizing amount of the coating. In general, amounts of from about 2 to about 30 weight percent, preferably from about 5 to about 20 weight percent, and most preferably about 10 to about 15 weight percent of coating (exclusive of any solvent) by weight of the bioabsorbable article contacted therewith is sufficient to provide significantly improved storage stability compared to that of the untreated article. As will be appreciated, the amount of composition and manner of application will vary depending upon the type of article and desired results.

The method of the invention can be practiced in conjunction with other known and conventional procedures such as sterilization e.g., by exposure to sterilizing gas or by radiation treatment. Known and conventional packaging techniques and materials are also contemplated. As previously stated, an advantage of the present invention lies in its ability to provide enhanced storage stability in a bioabsorbable article susceptible to hydrolytic degradation without having to eliminate all but a minuscule amount of moisture from the article and maintain the article in an especially dry environment until the final package sealing operation, as disclosed in U.S. Pat. Nos. 3,728,839 and 4,135,622. In fact, it is preferred that the article to be contacted with coating in accordance with this invention not receive the treatment described in the aforesaid patents.

The present invention will be described in greater detail by way of the following examples. In all cases, the moisture of the article was measured using a Mitsubishi Moisture Meter Model CA-05 with an attached Mitsubishi Water Vaporizer Model VA-05, in which heated, dry nitrogen (approximately 130° C. is swept across the sample and carries moisture therefrom to the moisture meter. In practice, the sample is transferred to the vaporizer as quickly as possible, on the order of about 5–10 sec., in order to minimize acquisition of moisture from the surrounding environment. All tests were performed at nominal room conditions, i. e., 70° F. and maximum 50% relative humidity.

EXAMPLE 1

A water-soluble collagen (available from Semex Medical Company, Frazer, Pa.) and glycerin (available from Baker Chemical Company, Phillipsburg, N.J.) were blended together in the following proportions:

| Ingredient | Weight Percent |
|---|---|
| collagen | 3 |
| glycerin | 97 |

The resulting blend formed a gel at 40° C. Injection molded bioabsorbable parts suitable for implantation into a living body and formed from a copolymer of glycolide-lactide were dipped into the gel at 40° C., with the resulting coatings on these parts then being allowed to dry. The dried coating comprised approximately 10% by weight of the dried article. The article was then equilibrated in an atmosphere having a dew point of −12° C. to a moisture content of 0.33% by weight of the article.

EXAMPLE 2

Gelatin (available from Fluka Chemical Company, Ronkonkoma, N.Y.) and having a Bloom strength of 60 grams, was dissolved in water to provide a concentration of 15% by weight gelatin in the water. The resulting solution was heated to 40° C., at which temperature the solution was liquid. Injection-molded bioabsorbable parts suitable for implantation into a living body and formed from a copolymer of glycolide-lactide were dipped into the resulting solution at this temperature. The coated parts were then vacuum dried, followed by equilibrating of the moisture content of the coating.

The procedure of this example was separately repeated in its entirety with two different grades of gelatin, one grade having a Bloom strength of 180 g. and the other grade having a Bloom strength of 250 g.

EXAMPLE 3

Gelatin (available from Kind & Knox Company, Sioux City, Iowa) having a 265 g. Bloom strength, glycerin (available from Baker Chemical Company, Phillipsburg, N.J.) and polyoxyethylene-polyoxypropylene surfactant of molecular weight 8350 and marketed under the trade name Poloxamer F-68 by BASF Wyandotte, Michigan, were all blended together in the following proportions:

| Ingredient | Weight Percent |
|---|---|
| gelatin | 82 |
| glycerin | 2 |
| surfactant | 16 |

The resulting blend was liquid at 40° C. Water was added to a level of 94% by weight of the resulting solution.

The resulting solution was sprayed at 40° C. with an air brush available from Badger Air-Brush Company, Franklin Park, Ill. onto injection molded bioabsorbable parts suitable for implantation into a living body. The bioabsorbable parts were formed from a copolymer of glycolide-lactide having a high glycolide content, e.g., about 90% glycolide.

After spraying, the parts were placed in a vacuum chamber and dried, resulting in a coating which was 8% by weight of the article. The article was equilibrated in an atmosphere having a dew point of −12° C., resulting in a moisture content of about 0.3% by weight of the article.

EXAMPLE 4

The procedure of Example 3 was repeated with the various ingredients being mixed in the following proportions.

| Ingredient | Weight Percent |
|---|---|
| gelatin | 72 |
| glycerin | 14 |
| surfactant | 14 |

Water was then added to a level of 94% by weight of the resulting solution, with the resulting solution then being sprayed at 40° C. onto the bioabsorbable parts with a Versa Glatt GPCG-1 fluidized bed coater available from Glatt Air Techniques, Inc., Ramsay, N.J. The coated articles were dried, resulting in a coating comprising 8% by weight of the coated article. The coated articles were sterilized by exposure to ethylene oxide gas, aerated to remove excess ethylene oxide, and equilibrated in an atmosphere having a dew point of −12° C. The moisture content of the sterile equilibrated articles was 0.3% by weight of the article.

What is claimed is:

1. A storage stable, bioabsorbable surgical device possessing improved storage stability and formed from a molded bioabsorbable article coated with a bioabsorbable composition, the composition comprising:

(i) about 98% to about 60% by weight gelatin;

(ii) about 1% to about 30% by weight of a plasticiser dispersed or dissolved in (i) said gelatin, wherein said plasticizer is a water-soluble hygroscopic polyhydroxy compound or ester derivative thereof; and (iii) about 0.1% to about 25% by weight of a polyethylene oxide-polypropylene oxide block copolymer surfactant dispersed or dissolved in (i) said gelatin or in (ii) said plasticizer;

wherein said surgical device is a surgical clip, stable, pin, screw, or tac fabricated in whole or in part from a polymer or copolymer of gylcolic acid, lactic acid, glycolide, lactide, dioxanone, trimethylene carbonate, caprolactone, polyalkylene glycol or combination thereof.

2. The device of claim 1 wherein said polyhydroxy compound or ester derivative thereof is selected from the group consisting of glycerol, monacetin, diacetin, ethylene glycol, diethylene glycol, triethylene glycol, 1,3-propanediol, trimethylolethane, trimethylol propane, pentaerythritol, sorbitol and mixtures thereof.

3. The device of claim 2 wherein said polyhydroxy compound is glycerol.

4. The device of claim 1 wherein (ii) said polyethylene oxide-polypropylene oxide block copolymer has the formula $$H(OCH_2CH_2)_x(OC_3H_6)_y(OCH_2CH_2)_zOH$$

wherein x is a number in the range from about 45 to about 90, y is a number in the range of from about 60 to about 85 and z is a number of from about 45 to about 90.

5. The device of claim 4 wherein said polyethylene oxide-polypropylene oxide block copolymer is $$H(OCH_2CH_2)_{75}(OC_3H_6)_{80}(OCH_2CH_2)_{50}OH.$$

6. The device of claim 5 wherein said compositioin comprises:

(i) about 90% to about 70% by weight of said gelatin;
(ii) about 5% to about 25% by weight of said plasticizer; and
(iii) about 1% to about 20% by weight of said surfactant.

7. The device of claim 6 wherein said composition comprises:

(i) about 85% to about 75% by weight of said gelatin;
(ii) about 10% to about 15% by weight of said plasticizer; and
(iii) about 5% to about 15% by weight of said surfactant.

8. The device of claim 1 additionally comprising at least one additive selected from the group consisting of antimicrobial agent, Human Growth Factor, magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system and mixtures thereof.

9. The device of claim 8 wherein said Human Growth Factor is selected from the group consisting of hEGF, TGF-beta, IGF, PDGF, FGF and mixtures thereof.

10. The device of claim 1 wherein said device is fabricated in whole or in part from a polymer or copolymer possessing short-chain polyester linkages or other readily hydrolyzable linkages.

11. The device of claim 1 wherein the plasticizer is water or glycerol.

12. The device of claim 1 wherein
said plasticizer (ii) is glycerol; and
said surfactant (iii) has the formula $$H(OCH_2CH_2)_x(OC_3H_6)_y(OCH_2CH_2)_zOH$$

wherein x is a number in the range of from about 45 to about 90, y is a number in the range of from about 60 to about 85 and z is a number in the range of from about 45 to about 90.

13. The surgical device of claim 1 wherein said device is a substantially rigid prothesis.

* * * * *